United States Patent

Heindel et al.

[11] Patent Number: 5,961,761
[45] Date of Patent: Oct. 5, 1999

[54] PROCESS OF PROVIDING MECHANICAL FASTENERS ON DISPOSABLE ABSORBENT ARTICLES

[75] Inventors: Timothy Raymond Heindel, Neenah; Tim Joseph Janssen, Kaukauna; Scott Lee Pennings; Gary Mack Reynolds, both of Neenah; Paul John Serbiak; Bruce Michael Siebers, both of Appleton; Robert Eugene Vogt, Neenah; Georgia Lynn Zehner, Larsen, all of Wis.

[73] Assignee: Kimberly-Clark Worldwide, Inc., Neenah, Wis.

[21] Appl. No.: 08/828,808

[22] Filed: Apr. 3, 1997

Related U.S. Application Data

[62] Division of application No. 08/791,691, Jan. 30, 1997, abandoned, which is a continuation of application No. 08/335,527, Nov. 7, 1994, abandoned.

[51] Int. Cl.$^6$ .............................. B32B 31/00; A61F 13/15
[52] U.S. Cl. .............................. 156/163; 156/66; 156/164; 604/391
[58] Field of Search .................................. 604/389, 390, 604/391, 385.1; 156/66, 161, 163, 164, 229, 494

[56] References Cited

U.S. PATENT DOCUMENTS

| | | | |
|---|---|---|---|
| 2,068,456 | 1/1937 | Hooper | 154/2 |
| 4,389,212 | 6/1983 | Tritsch | 604/389 |
| 4,518,451 | 5/1985 | Luceri et al. | 156/202 |
| 4,633,565 | 1/1987 | DeWoskin | 29/417 |
| 4,761,322 | 8/1988 | Raley | 428/198 |
| 4,881,997 | 11/1989 | Hatch | 156/66 |
| 4,894,060 | 1/1990 | Nestegard | 604/391 |
| 4,909,870 | 3/1990 | Gould et al. | 156/66 |
| 4,933,224 | 6/1990 | Hatch | 428/100 |
| 4,988,551 | 1/1991 | Zegler | 428/40 |
| 4,999,067 | 3/1991 | Erb et al. | 156/73.1 |
| 5,176,670 | 1/1993 | Roessler et al. | 604/391 |
| 5,246,656 | 9/1993 | Stephenson et al. | 264/153 |

FOREIGN PATENT DOCUMENTS

WO92/20251  11/1992  European Pat. Off. .

*Primary Examiner*—Ronald Stright
*Assistant Examiner*—David J. Cho
*Attorney, Agent, or Firm*—Jeffrey B. Curtin

[57] ABSTRACT

Disclosed is an improved process for attaching and protecting a mechanical fastener on a disposable absorbent article and a disposable absorbent article produced by the same. The process comprises the following steps: (1) providing a disposable absorbent article which includes an outer cover, a bodyside liner, and an absorbent core disposed between the outer cover and the bodyside liner; (2) providing a mechanical fastener which includes a first fastening element; (3) attaching the first fastening element of the mechanical fastener to the disposable absorbent article; (4) releasably engaging the first fastening element with the disposable absorbent article to protect the first fastening element; and (5) subsequently packaging the disposable absorbent article for commercial sale. The first fastening element and a portion of the disposable absorbent article may be releasably engaged by constrictively passing them between a pair of rotatable nip rolls. In a particular aspect, the first fastening element is the hook material of a hook-and-loop type mechanical fastener.

26 Claims, 9 Drawing Sheets

PROCESS OF PROVIDING MECHANICAL FASTENERS ON DISPOSABLE ABSORBENT ARTICLES

This application is a divisional of application Ser. No. 08/791,691 entitled "PROCESS OF PROVIDING MECHANICAL FASTENERS ON DISPOSABLE ABSORBENT ARTICLES" and filed in the U.S. Patent and Trademark Office on Jan. 30, 1997, which is a continuation of application Ser. No. 08/335,527 filed Nov. 7, 1994, both now abandoned. The entirety of this application is hereby incorporated by reference.

BACKGROUND OF THE INVENTION

The use of mechanical fastening means on disposable absorbent articles, such as diapers, training pants, adult incontinent products, feminine care products, and the like, are well known. A common type of mechanical fastener employed on disposable absorbent articles is a hook-and-loop type fastener in which a hook or hook-like element is provided which is adapted for releasably engaging with a loop or loop-like material. Such hook-and-loop type fasteners are also well known in the prior art. Other well known types of mechanical fasteners include snaps, buttons, zippers, mushroom fasteners and the like.

While the use of mechanical fasteners, such as hook-and-loop type fasteners, on disposable absorbent articles is known, such use has not become widespread. This is due, in part, to the increased cost of such mechanical fasteners relative to the more common adhesive tapes currently used on disposable absorbent articles. An additional reason that mechanical fasteners have not been widely used on disposable absorbent articles relates to the difficulty of forming and controlling such fasteners at the high speeds generally associated with the manufacture of disposable absorbent articles. The process issues associated with the formation of such mechanical fasteners also affects the relative cost of such fasteners.

The process difficulties associated with the mechanical fasteners relates not only to the formation and attachment of the mechanical fasteners to other elements of the disposable absorbent articles but also to the control and protection of the mechanical fasteners as the absorbent article is manufactured and packaged. This is particularly true when trying to form and control hook-and-loop type fasteners. For example, the hook material must be controlled and protected to reduce or eliminate damage to the hook material during the manufacturing and packaging processes. Thus, in order to render the use of mechanical fasteners, such as hook-and-loop type fasteners, on disposable absorbent articles more feasible, it is desirable to provide improved processes for the control and protection of such fasteners.

SUMMARY OF THE INVENTION

In response to the discussed difficulties and problems encountered in the prior art, a new process for attaching and protecting mechanical fasteners on disposable absorbent articles and a disposable absorbent article produced by the same has been discovered.

In one aspect, the present invention concerns a process for attaching a mechanical fastener to a disposable absorbent article and protecting said mechanical fastener before said disposable absorbent article is handled by a user. The process comprises the following steps: (1) providing a disposable absorbent article which includes an outer cover, a bodyside liner, and an absorbent core disposed between the outer cover and the bodyside liner; (2) providing a mechanical fastener which includes a first fastening element; (3) attaching the first fastening element of the mechanical fastener to the disposable absorbent article; (4) releasably engaging the first fastening element with the disposable absorbent article to protect the first fastening element; and (5) subsequently packaging the disposable absorbent article for commercial sale. In a particular aspect of the invention, the first fastening element and a portion of the disposable absorbent article are releasably engaged by passing them between a pair of rotatable nip rolls.

In another aspect, the invention concerns a process for attaching a hook material of a hook-and-loop type mechanical fastener to a disposable absorbent article and protecting the hook material before the disposable absorbent article is handled by a user. The process comprises the following steps: (1) providing a disposable absorbent article which includes an outer cover, a bodyside liner, and an absorbent core disposed between the outer cover and the bodyside liner; (2) providing the hook material which includes a base sheet and stemlike projections which extend from the base sheet; (3) attaching the base sheet of the hook material to the disposable absorbent article; (4) releasably engaging the stemlike projections with the disposable absorbent article to protect the hook material; and (5) subsequently packaging the disposable absorbent article for commercial sale. In a particular aspect of the invention, the disposable absorbent article includes at least one ear tab and the base sheet of the hook material is attached to the ear tab.

In another aspect, the invention concerns a disposable absorbent article which includes an outer cover, a bodyside liner, an absorbent core disposed between the outer cover and the bodyside liner and at least one hook-and-loop type mechanical fastener which includes a hook material. The disposable absorbent article is produced by a process which comprises the following steps: (1) providing the hook material which includes a base sheet and stemlike projections which extend from the base sheet; (2) attaching the base sheet of the hook material to the disposable absorbent article; (3) releasably engaging the stemlike projections of the hook material with the disposable absorbent article to protect the stemlike projections before the disposable absorbent article is handled by a user; and (4) subsequently packaging the disposable absorbent article for commercial sale.

In still another aspect, the invention concerns a package of disposable absorbent articles which comprises a plurality of the disposable absorbent articles. Each of the disposable absorbent articles includes an outer cover, a bodyside liner, an absorbent core disposed between the outer cover and the bodyside liner, and at least one mechanical fastener. The mechanical fastener is releasably engaged with the disposable absorbent article to protect the mechanical fastener before the disposable absorbent article is handled by a user. In a particular aspect of the invention, the mechanical fastener is a hook-and-loop type mechanical fastener which comprises a hook material. The hook material includes a base sheet and stemlike projections which extend from the base sheet. The stemlike projections of the mechanical fastener are releasably engaged with the disposable absorbent article to protect the hook material before the disposable absorbent article is handled by a user.

In yet another aspect, the present invention concerns a package of a plurality of disposable absorbent articles. Each of the disposable absorbent articles includes an outer cover, a bodyside liner, an absorbent core disposed between the outer cover and the bodyside liner, and at least one hookand-loop type mechanical fastener. The hook-and-loop fastener includes a hook material which includes a base sheet and stemlike projections which extend from the base sheet. The stemlike projections are releasably engaged with the disposable absorbent article to protect the hook material and provide a pant-like structure before the disposable absorbent article is handled by a user.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the appended claims.

DETAILED DESCRIPTION OF THE INVENTION

The present invention relates to a process for attaching and protecting a mechanical fastener on a disposable absorbent article and a disposable absorbent article produced by the same. The term "disposable absorbent article" is intended to refer to any disposable article intended to absorb discharged body fluids. Examples of disposable absorbent articles include diapers, adult incontinence products, training pants, feminine napkins, wound dressings, and the like. For ease of understanding, much of the following description of the present invention will be made in terms of the process of attaching and protecting mechanical fasteners on disposable diapers and the disposable diapers made by such processes. Nonetheless, it is to be understood that the process of attaching and protecting mechanical fasteners of the present invention is equally suited for use in manufacturing any other disposable absorbent article.

In one embodiment, the present invention refers to a process for attaching and protecting mechanical fasteners on disposable absorbent articles. For example, the process may be used to attach mechanical fasteners to a disposable diaper such as that representatively illustrated in FIGS. 1–8. Those skilled in the art will recognize that the disposable diaper 20 generally comprises an outer cover 22, an inner bodyside liner 24, and an absorbent core 26 located between the outer cover 22 and the bodyside liner 24. Leg elastics 28 are located generally at the longitudinal edges of the diaper 20. The disposable diaper 20 may further comprise a front waist elastic 30 and a rear waist elastic 32. As representatively illustrated, the disposable diaper 20 also includes mechanical fasteners 34 and 36.

The outer cover 22 of the disposable diaper 20, as representatively illustrated in FIGS. 1–8, may suitably be composed of a material which is either liquid permeable or liquid impermeable. It is generally preferred that the outer cover 22 be formed from a material which is substantially impermeable to liquids. For example, a typical outer cover can be manufactured from a thin plastic film or other flexible liquid-impermeable material. For example, the outer cover 22 may be formed from a polyethylene film having a thickness of from about 0.012 millimeter (0.5 mil) to about 0.051 millimeter (2.0 mils). If it is desired to present the outer cover 22 with a more clothlike feeling, the outer cover 22 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 22 may be formed of a woven or nonwoven fibrous web layer which has been totally or partially constructed or treated to impart a desired level of liquid impermeability to selected regions that are adjacent or proximate the absorbent core 26. Still further, the outer cover 22 may optionally be composed of a micro-porous "breathable" material which permits vapors to escape from the absorbent core 26 while still preventing liquid exudates from passing through the outer cover 22. The outer cover may be formed from an elastic material such as elastomeric films, e.g., natural or synthetic rubber; elastomeric foams, e.g., urethane foams; elastomeric nonwoven materials; laminates or composites of such elastomeric materials with other elastomeric or non-elastomeric materials, e.g., neck-bonded laminates or stretch-bonded laminates; and the like.

The bodyside liner 24 of the disposable diaper 20, as representatively illustrated in FIGS. 1–8, suitably presents a bodyfacing surface which is compliant, soft feeling and nonirritating to the wearer's skin. Further, the bodyside liner 24 may be less hydrophilic than the absorbent core 26, to present a relatively dry surface to the wearer, and may be sufficiently porous to be liquid permeable, permitting liquid to readily penetrate through its thickness. A suitable bodyside liner 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 24 is suitably employed to help isolate the wearer's skin from liquids held in the absorbent core 26.

Various woven and nonwoven fabrics can be used for the bodyside liner 24. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 24 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation Triton X-102.

Specific examples of disposable diapers on which the process of the present invention may be utilized are disclosed in the following U.S. patents and U.S. patent Applications: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemer et al.; U.S. Pat. No. 5,192,606 issued Mar. 9, 1993, to Proxmire et al., and U.S. patent application Ser. No. 08/096,654 filed Jul. 22, 1993, in the name of Hanson et al.

As representatively illustrated in FIGS. 1–8, the disposable diaper 20 includes mechanical fasteners 34 and 36. The mechanical fasteners 34 and 36, as representatively illustrated in FIGS. 1–8, include one component of a hook-and-loop type mechanical fasteners as are well known to those skilled in the art. Other fasteners which may be used in the present invention include cohesive materials, snaps, buttons and the like. As used herein, reference to a mechanical fastener refers to at least one component of a combination of a first fastening element which is adapted to mechanically interlock with a second fastening element. For example, the first and second fastening elements of the mechanical fasteners may include the hook material and loop material of a hook-and-loop type fastener or the male and female snap portions of a snap type fastener.

For ease of understanding, much of the following description of the present invention will be made in terms of the process of attaching and protecting hook-and-loop type mechanical fasteners on disposable diapers. Nonetheless, it is to be understood that the process described is equally suited for use in attaching and protecting any other type of mechanical fasteners.

Hook-and-loop type fasteners are known to those skilled in the art. The mechanical fasteners 34 and 36, as representatively illustrated in FIGS. 1–8, generally comprise a hook material 40 and/or a loop material 42. The mechanical fasteners 34 and 36 may also include a fingertab 44 to improve the ease of fastening and refastening. As representatively illustrated in FIGS. 3, 5 and 7, the hook material 40 generally comprises a base sheet material 46 from which stemlike projections 48 extend. One end of each stemlike projection 48 is attached to the base sheet material 46, while the other end of the stemlike projection 48 defines a hook, or hook-like structure, which is adapted to engage and interlock with a loop or loop-type material. The loop or loop-type material 42 generally comprises a woven or nonwoven material defining individual loops of material which can interlock with the hook or hook-like material 40.

Exemplary of a hook material 40 suitable for use in the present invention is that obtained from Velcro Group Company, Manchester, N.H., under the trade designation CFM-22 and CFM-15. Suitable hook materials generally comprise from about 300 to about 1000 hooks per square inch (about 46 to about 155 hooks per square centimeter), preferably from about 700 to about 900 hooks per square inch (about 108 to about 140 hooks per square centimeter). The hooks suitably have a height of from about 0.015 inch (0.038 centimeter) to about 0.050 inch (0.127 centimeter), preferably of from about 0.025 inch (0.0635 centimeter) to about 0.035 inch (0.0889 centimeter).

Exemplary of a loop material 42 suitable for use in the present invention is that obtained from Guilford Mills, Inc., Greensboro, N.C., under the trade designation Style 19902 or Style 30020. A suitable loop material is a fabric of a raised loop construction, stabilized through napping and thermosetting such that the loops are erect from the base material. The fabric may be a two bar warp knit construction having from 21 to 41 courses per inch (8.27 to 16.4 courses per centimeter) and from 26 to 46 wales per inch (10.24 to 18.1 wales per centimeter), preferably of polyester yarn, in which 15–35 percent of the yarn is composed of yarn having about 15 or less filaments and having a yarn denier (d) within the range of about 15–30 d. In addition, about 65–85 percent of the yarns are those having 1–30 individual filaments therein and having a yarn denier within the range of about 30–50 d. The caliper is 0.010 to 0.040 inch (0.0254 to 0.1 centimeter) and basis weight from 1.0 to 3.0 ounces per square yard. Suitable loop materials also include stitch bonded materials, needled materials, nonwoven materials, laminates of a nonwoven material and a film material; malimo composites (available from Tietex and Milliken both of Spartenburg, S.C.) and the like. Other suitable loop materials are shown, for example, in U.S. Pat. No. 5,019,073 issued May 28, 1991, to Roessler et al., the disclosure of which is incorporated by reference herein.

In general, the first fastening element or hook material 40 will be attached to the rear periphery of the disposable diaper 20, and the second fastening element or loop material 42 will be attached to the outer surface of the disposable diaper 20, near a front edge of the diaper. Alternatively, the hook material 40 may be attached to the front periphery of the disposable diaper 20, and the loop material may be attached to the outer surface of the disposable diaper 20, near a rear edge of the diaper. Those skilled in the art will appreciate that the loop material 42, with which the hook material 40 is intended to engage, will be positioned on the disposable diaper 20 such that the mechanical fasteners 34 and 36 can be utilized to attach the disposable diaper 20 about the waist of a wearer.

As representatively illustrated in FIGS. 1–8, the disposable diaper 20 of the present invention may also include at least one ear tab 38. Typically, the ear tab 38 is attached to the rear periphery of the diaper 20. In such a configuration, the hook material 40, can be attached to the ear tab 38. The ear tab 38 car be made of any material which provides the desired fastening of the disposable diaper 20 about the waist of the wearer. Suitably, the ear tab 38 may be formed out of a material such as that used to form the outer cover and/or body-side liner. Suitable materials from which the ear tab may be formed include films, nonwoven materials, woven or knit materials, foams, and composites and laminates of the above materials. The ear tab may be formed from an elastic material such as elastomeric films, e.g., natural or synthetic rubber; elastomeric strands, e.g., Lycra™ strands; elastomeric foams, e.g., urethane foams; elastomeric nonwoven materials; laminates or composites of such elastomeric materials with other elastomeric or non-elastomeric materials, e.g., neck-bonded laminates or stretch-bonded laminates; and the like. When the ear is formed from an elastic material, the elastic material can suitably be elongated to from about 75 percent to about 150 percent of its relaxed length, more specifically from about 100 percent to about 150 percent of its relaxed length. Elongations within these ranges are believed to result in the best fit in use.

In another embodiment, the present invention concerns a process for attaching mechanical fasteners to disposable absorbent articles and protecting the mechanical fasteners before the articles are handled by a user. To eliminate the risk of damage which can adversely impact the functioning of the mechanical fasteners, each mechanical fastener 34 and 36 must be effectively protected as the disposable absorbent article, such as the disposable diaper 20 illustrated in FIGS. 1–8, is manufactured and packaged. The process of the invention can best be understood by reference to the drawings wherein FIG. 9 illustrates a schematic view of a process according to the present invention. The process will be described in terms of attaching a hook material of a hook-and-loop type mechanical fastener to a substrate web and protecting the hook material. However, it is to be understood that the process is equally suited for attaching and protecting any type of mechanical fastener to any type of substrate web. For example, the substrate web may be the disposable diaper 20 or any components of the disposable diaper 20, such as the outer cover 22 or bodyside liner 24, as representatively illustrated in FIGS. 1–8. In a particular embodiment, the process may be used to apply mechanical fasteners to the outer cover 22 or bodyside liner 24 before they are joined together to form the disposable diaper 20.

As representatively illustrated in FIG. 9, a generally continuous length of a hook material 50 is provided. Typically, the hook material 50 has a base material and stemlike projections which extend from the base material. The hook material 50 may be used to provide the hook portion of the hook-and-loop type mechanical fasteners 34 and 36 as representatively illustrated in FIGS. 1–8. A substrate web 52 is provided from a supply roll. The base material of the hook material 50 is attached to the substrate web 52 with the stemlike projections extending away from the substrate web 52. Any method capable of joining different materials together is believed suitable for use in the present invention. For example, the base material of the hook material 50 may be attached to the substrate web 52 by hot or cold melt adhesives, thermal bonding (including ultrasonic bonding), sewing, combinations of these methods, and the like. In one preferred embodiment of the present invention, the hook material 50 is attached to the substrate web 52 with both adhesive and thermal bonds. Exemplary of suitable adhesive materials are those commercially available from Findley Adhesives, Inc., Wauwatosa, Wis., under the trade designation H-2096.

The composite of the hook material 50 and the substrate web 52 is then cut by a cutter 54 to form individual fastening elements 56. Those skilled in the art will recognize that cutter 54 may comprise rotary cutters, air knives, thermal knives, pinch cutters, ultrasonic cutters, lasers, and the like. The individual fastening elements 56 are then folded in the folding area 58 about a fold line 60. The folding area 58 suitably contains folding boards, plows, and the like, to effectuate the described folding as are well known to those skilled in the art. After the fastening elements 56 are folded over, the stemlike projections of the hook material 50 and the substrate web 52 are releasably engaged by constrictively passing between a pair of rotatable nip rolls 62. The pressure exerted by the nip rolls 62 is any amount sufficient to provide the desired engagement. For example the pressure exerted may be at least about 70 pounds per linear inch and desirably from about 70 to about 180 pounds per linear inch.

The rotatable nip rolls 62 may be of any configuration which provides the desired engagement between the stemlike projections of the hook material 50 and the substrate web 52. For example, the rotatable nip rolls 62 may have a smooth or rough surface. In a particular embodiment as representatively illustrated in FIG. 9, at least one of the rotatable nip rolls 62 has a plurality of pins extending radially outward from its circumferential surface. The pins can improve the engagement between the stemlike projections of the hook material 50 and the substrate web 52. For example, the pins can force the stemlike projections further into the substrate web 52 to provide improved engagement.

Figure 9:
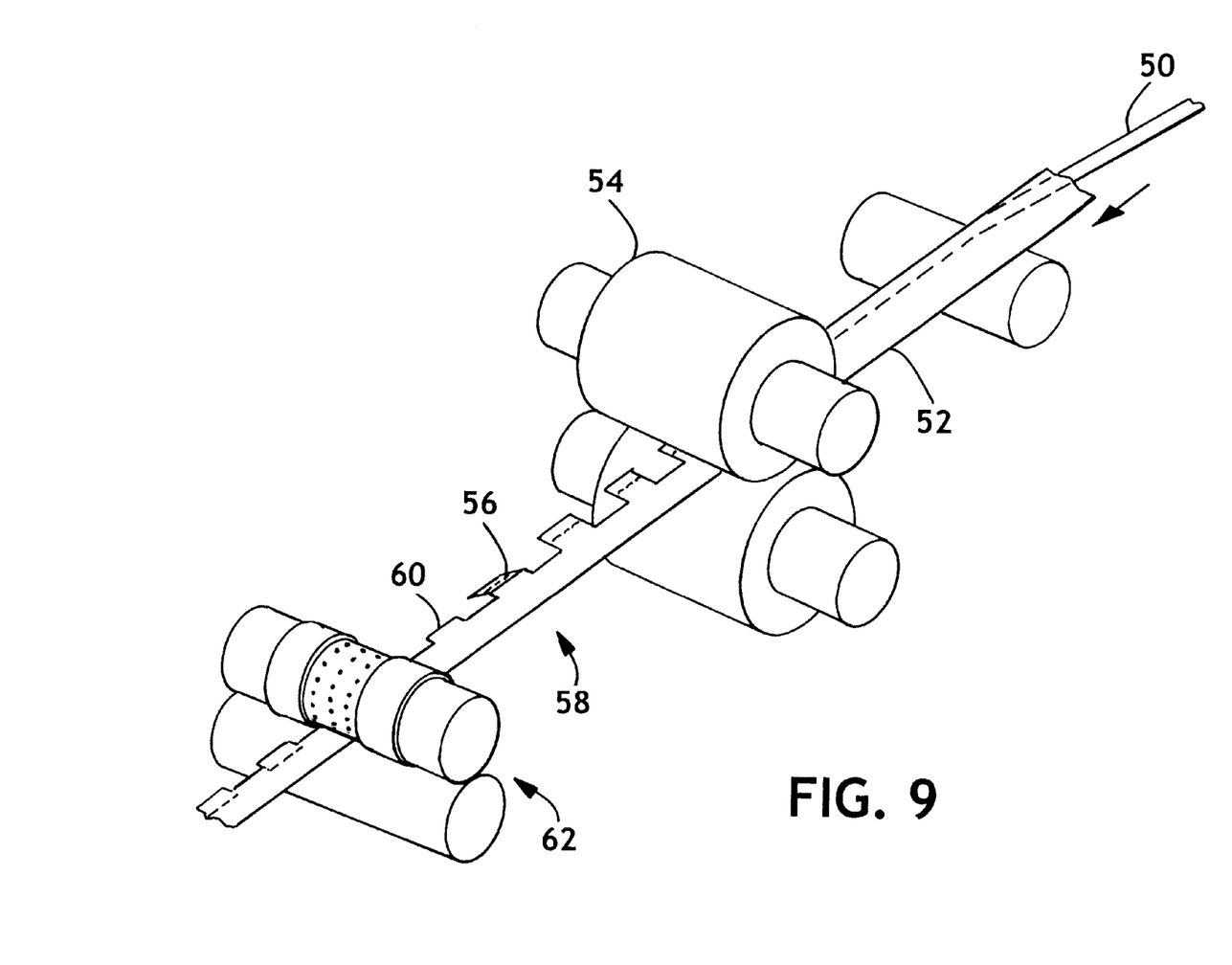
FIG. 9 schematically illustrates an embodiment of a process of the present invention.
Figure 10:
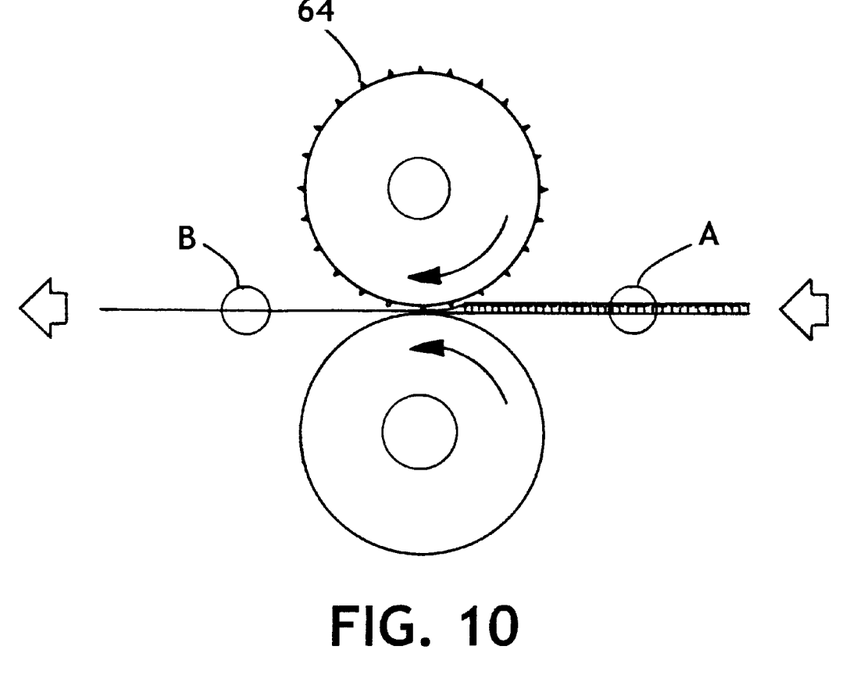
FIG. 10 illustrates the nip rolls illustrated in FIG. 9.
Figure 10A:
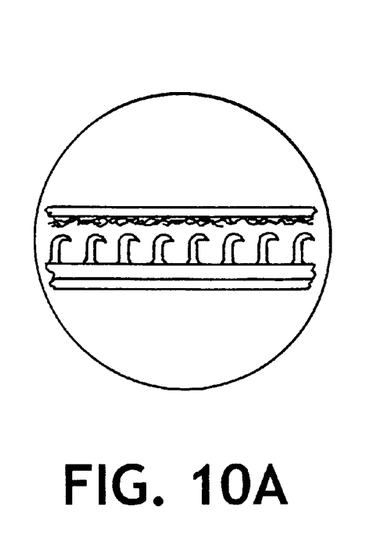
FIG. 10A is an enlarged view of the area in circle A in FIG. 10.
Figure 10B:
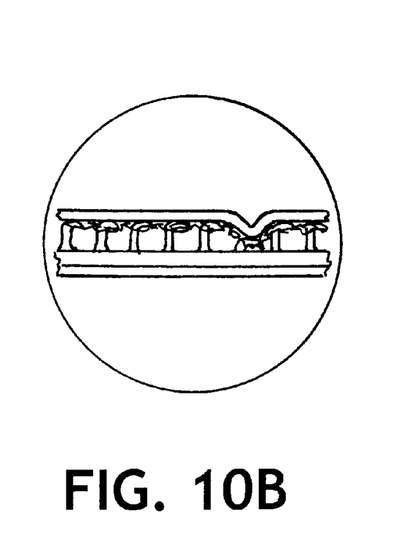
FIG. 10B is an enlarged view of the area in circle B in FIG. 10.

This aspect of the invention is illustrated in FIGS. 10, 10A and 10B. FIG. 10 illustrates the nip rolls 62 illustrated in FIG. 9. The pins 64 are illustrated on the outer surface of one of the nip rolls. FIG. 10A illustrates an enlarged view of the area from circle A in FIG. 10 showing a hook and loop material prior to engagement. FIG. 10B illustrates an enlarged view of the area from circle B in FIG. 10 showing a hook and loop material after engagement caused by the pins 64.

Figure 11:
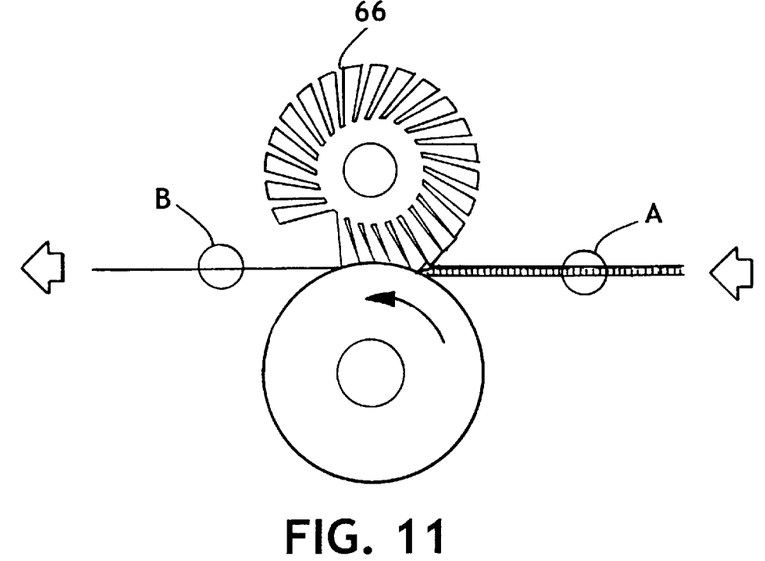
FIG. 11 illustrates an alternative embodiment of the nip rolls illustrated in FIG. 9.
Figure 11A:
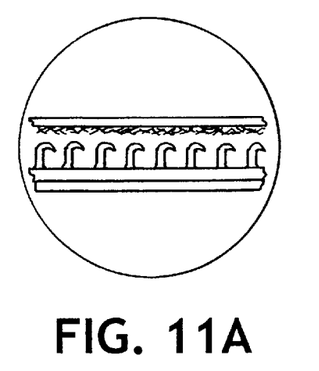
FIG. 11A is an enlarged view of the area in circle A in FIG. 11.
Figure 11B:
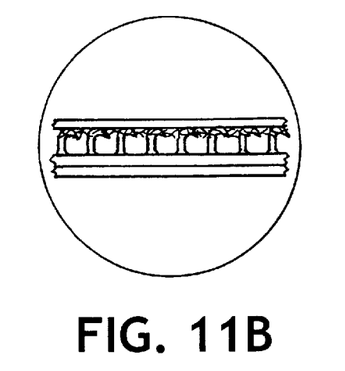
FIG. 11B is an enlarged view of the area in circle B in FIG. 11.

Alternatively, at least one of the rotatable nip rolls 62 may have a plurality of grooves or slots arranged in a cross directional configuration about its circumferential surface. Such a grooved nip roll can function to provide a scrubbing or scuffing action to releasably engage the stemlike projections of the hook material 50 and the substrate web 52 without adversely affecting or damaging the hook material 50. FIG. 11 illustrates nip rolls 62 according to this alternative embodiment. FIG. 11 illustrates a nip roll with grooves or slots 66. FIG. 11A illustrates an enlarged view of the area from circle A in FIG. 11 showing a hook and loop material prior to engagement. FIG. 11B illustrates an enlarged view of the area from circle B in FIG. 11 showing a hook and loop material after engagement caused by the scrubbing or scuffing action of the grooves 66 in the nip rolls 62.

The engagement of the stemlike projections of the hook material 50 with the substrate web 52 must be sufficient to protect and control the hook material 50 as the composite is further manufactured and packaged for consumer sale. For example, the hook material 50 on the individual fastening elements 56 can tend to flutter at high manufacturing speeds which may damage the stemlike projections of the hook material 50.

The process of the present invention, as representatively illustrated in FIG. 9, may be used to provide a disposable diaper, such as those representatively illustrated in FIGS. 2–8 wherein the hook material 40 of the hook-and-loop type mechanical fasteners 34 and 36 has been protected and controlled during the manufacturing and packaging processes. Specifically, it is important that the hook material 40 be protected up until the point in time at which the disposable diaper 20 is handled by the user. To ensure proper fastening and refastening about a wearer, the stemlike projections 48 of the hook material 40 of the hook-and-loop type mechanical fasteners 34 and 36 must not be damaged during the manufacturing and packaging processes.

FIGS. 2–8 representatively illustrate several different embodiments of the present invention wherein the hook material 40 of the hook-and-loop type mechanical fasteners 34 and 36 of the disposable diapers 20 has been controlled and protected. The disposable diapers 20 include an outer cover 22, a bodyside liner 24, an absorbent core 26 disposed between the outer cover 22 and bodyside liner 24, a pair of ear tabs 38, and a pair of mechanical fasteners 34 and 36. The mechanical fasteners 34 and 36 include a hook material 40 and a loop material 42 which are attached to the disposable diaper 20. The mechanical fasteners 34 and 36 may also include a fingertab 44. One skilled in the art will recognize that certain components of the disposable diapers 20 may be omitted such as the ear tabs 38 and fingertabs 44, as representatively illustrated in FIGS. 2–8. In the illustrated embodiments, the hook material 40 of the hook-and-loop type mechanical fasteners 34 and 36 is releasably engaged with the disposable diaper 20 to protect the hook material 40 before the disposable diaper 20 is handled by a user.

The hook material 40 may be releasably engaged with the disposable diaper 20 or any component of the disposable diaper 20 by any suitable process such as that representatively illustrated in FIG. 9. For example, the hook material 40 and a portion of the disposable diaper 20 may be releasably engaged by passing between a pair of rotatable nip rolls 62, as representatively illustrated in FIG. 9.

Figure 1:
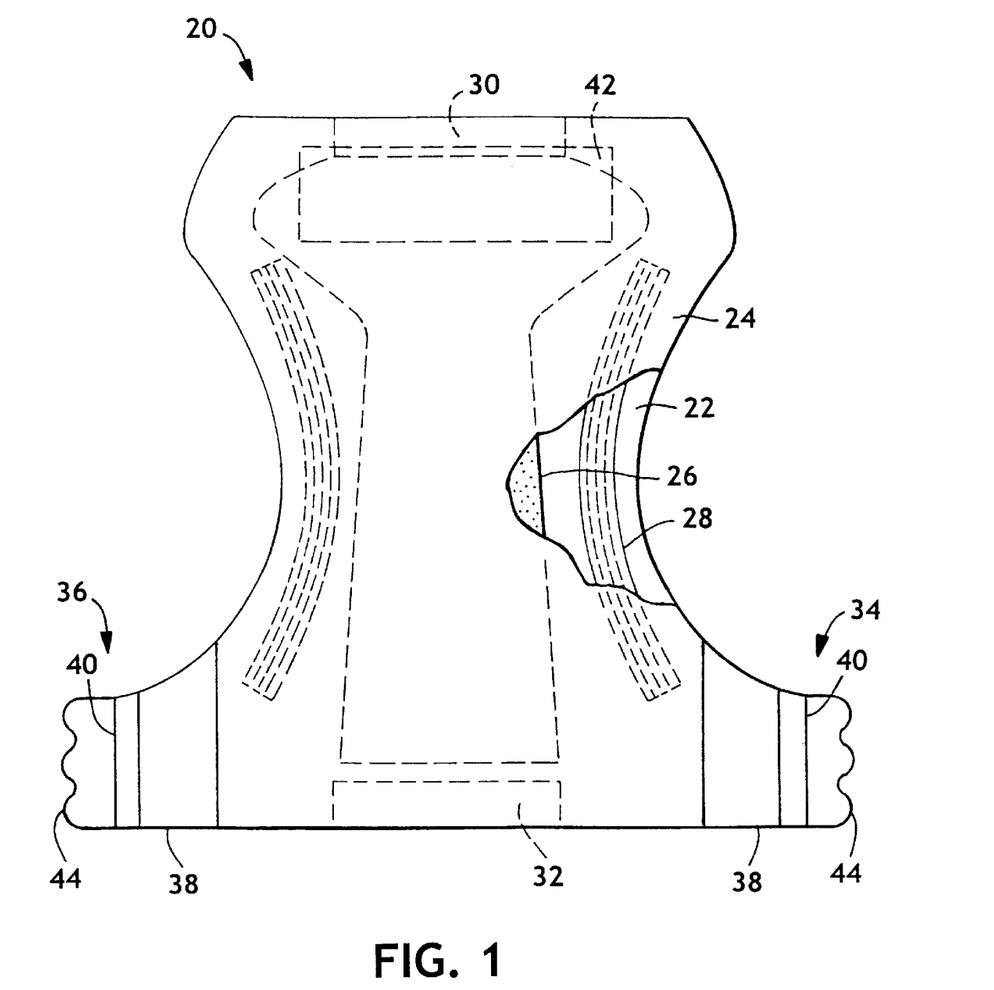
FIG. 1 is a partially cut away plan view of an absorbent article having mechanical fasteners according to the present invention.
Figure 2:
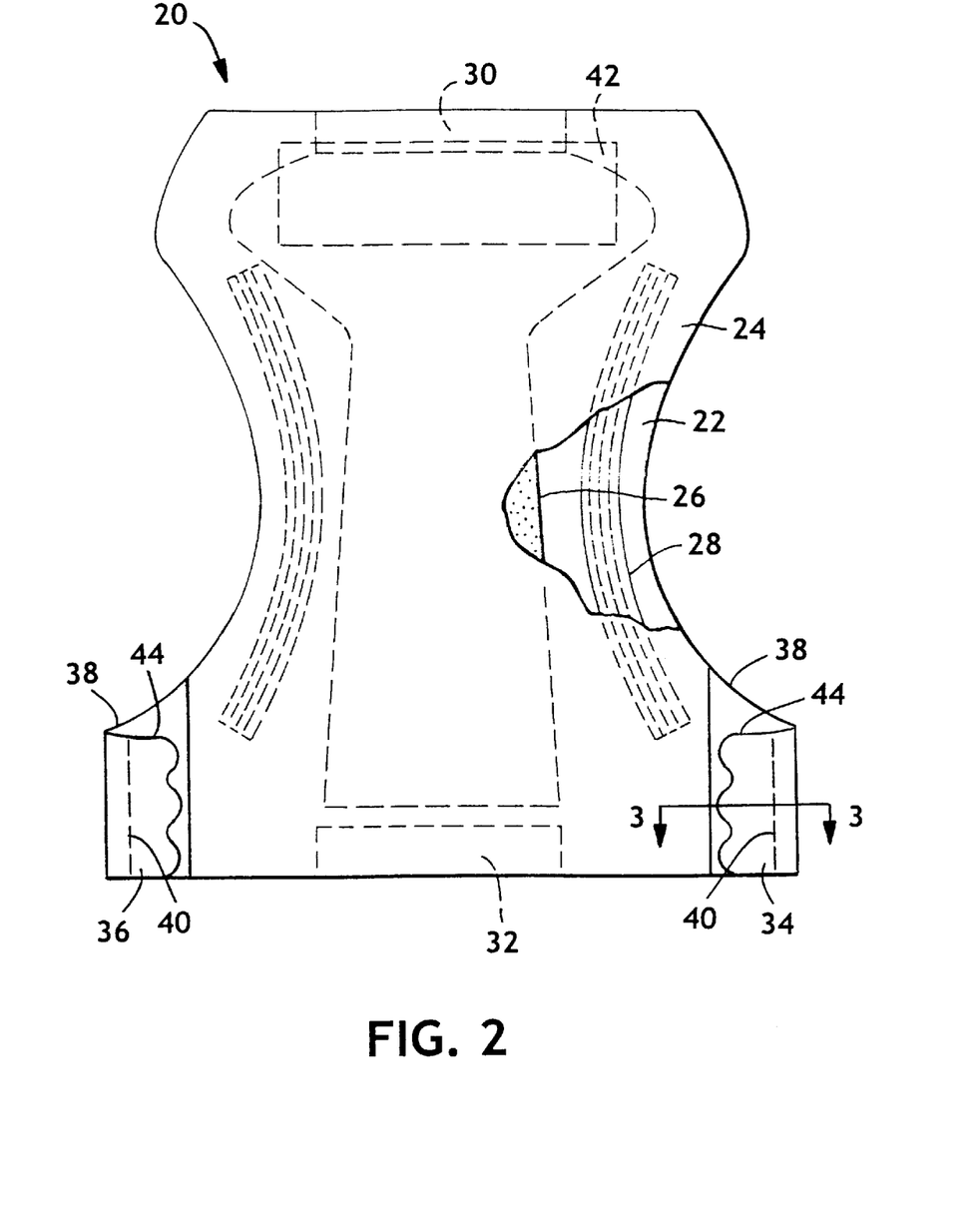
FIG. 2 is a partially cut away plan view of an absorbent article according to the present invention which illustrates an attachment of the mechanical fasteners of the present invention.
Figure 3:
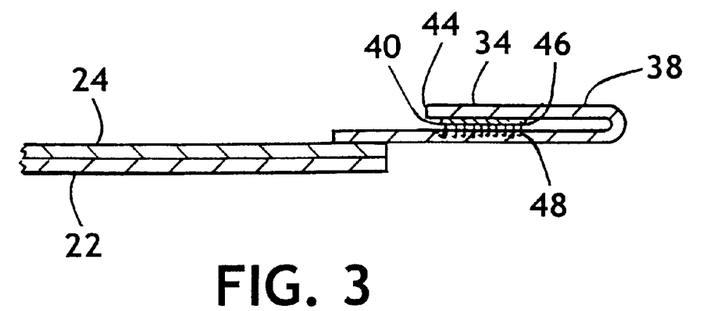
FIG. 3 is a cross-sectional view of the attachment of the mechanical fasteners as illustrated in FIG. 2 taken along line 3—3.

In one embodiment, as representatively illustrated in FIGS. 2 and 3, the hook material 40 may be folded over and releasably engaged with the ear tabs 38 to protect the hook material 40 before the disposable diaper 20 is further manufactured and packaged for commercial sale. Alternatively, as representatively illustrated in FIGS. 4 and 5, the hook material 40 may be folded over and releasably engaged with the bodyside liner 24 of the disposable diaper 20. As illustrated in FIGS. 3 and 5, the stemlike projections 48 which extend from the base sheet 46 of the hook material 40 are releasably engaged with the ear tab 38 or bodyside liner 24.

Figure 6:
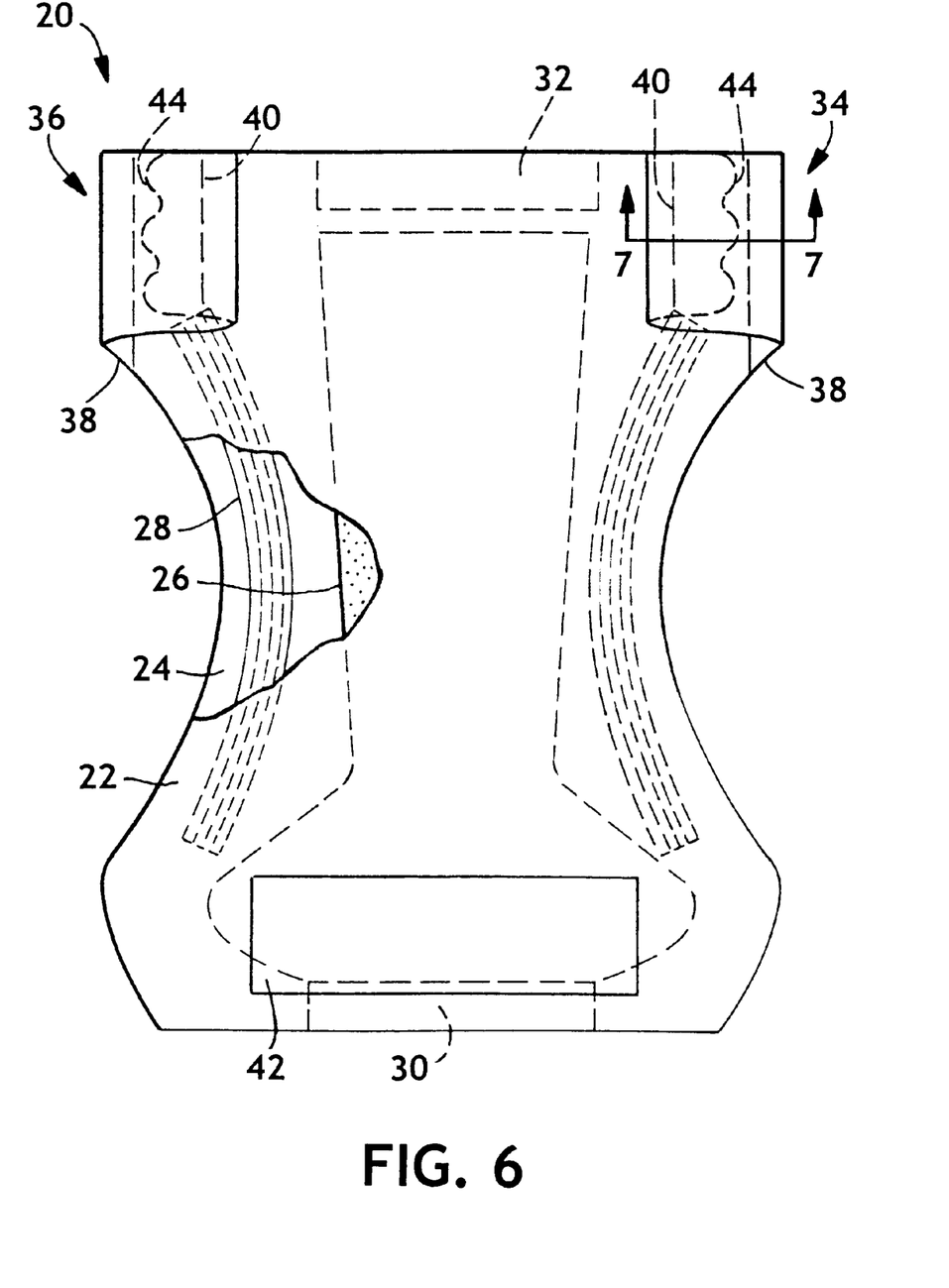
FIG. 6 is a partially cut away plan view of an absorbent article according to the present invention which illustrates an alternative attachment of the mechanical fasteners of the present invention.
Figure 7:
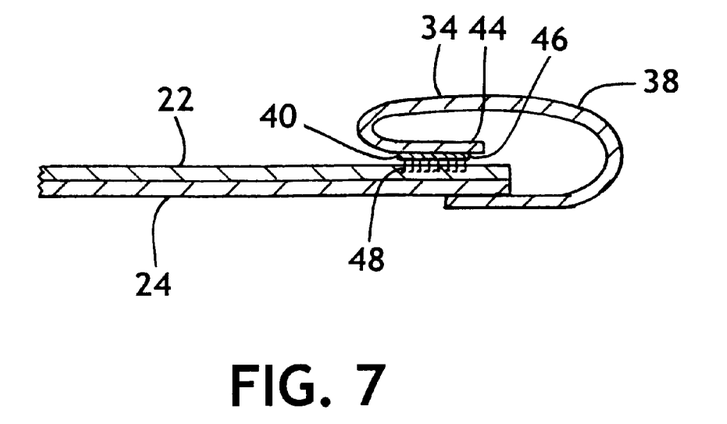
FIG. 7 is a cross-sectional view of the attachment of the mechanical fasteners as illustrated in FIG. 6 taken along line 7—7.

In another embodiment as representatively illustrated in FIGS. 6 and 7, the hook material 40 may be folded over and releasably engaged with the outer cover 22 of the disposable diaper 20 to protect the hook material 40 before the disposable diaper 20 is further manufactured and packaged for commercial sale. As illustrated in FIG. 7, the stemlike projections 48 which extend from the base sheet 46 of the hook material 40 are releasably engaged with the outer cover 22 of the disposable diaper 20.

Figure 8:
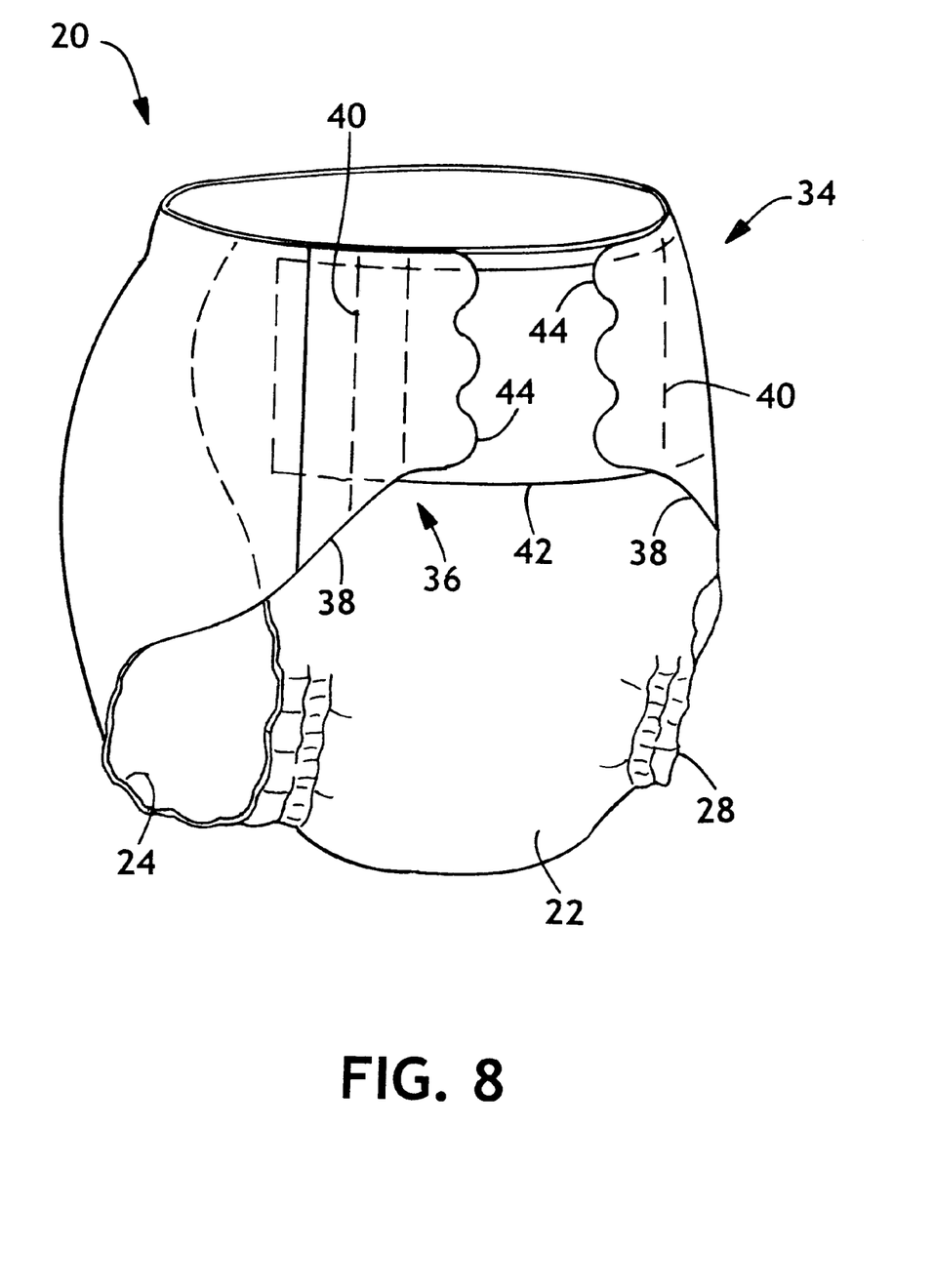
FIG. 8 is a perspective view of an absorbent article according to the present invention which illustrates an alternative attachment of the mechanical fasteners of the present invention.

In still another embodiment as representatively illustrated in FIG. 8, the hook material 40 may be releasably engaged with the outer cover 22 or loop material 42 of the disposable diaper 20 in a manner to provide a pant-like structure and protect the hook material 40 before the disposable diaper 20 is further manufactured and packaged for commercial sale.

The disposable diaper 20 of the different embodiments of the present invention may also include one or more patches of loop material located in any desired location to releasably engage with the stemlike projections 48 of the hook material 40. For example, a patch of loop material may be located on the ear tab 38, outer cover 22 or bodyside liner 24 of the disposable diaper 20 to releasably engage with the stemlike projections 48 of the hook material 40 to protect the hook material 40 as the disposable diaper 20 is manufactured and packaged.

In still another embodiment, the present invention provides a package which includes a plurality of disposable absorbent articles such as the disposable diapers representatively illustrated in FIGS. 2–8. The package may include at least about 1 and desirably from about 10 to about 96 disposable absorbent articles. Each of the disposable absorbent articles in the package includes mechanical fasteners which are attached and protected according to the different embodiments of the present invention. For example, wherein the mechanical fasteners are hook-and-loop type fasteners as illustrated in FIGS. 2–8, the hook material 40 of the mechanical fasteners 34 and 36 is releasably engaged with the disposable diapers 20 to protect the hook material 40 before the disposable absorbent articles are handled by the user.

In the different embodiments of the present invention as representatively illustrated in FIGS. 1–9, the releasable engagement of the hook material 40 of the mechanical fasteners 34 and 36 with the disposable diaper 20 must be sufficient to ensure adequate protection of the mechanical fasteners 34 and 36. Specifically, the stemlike projections 48 of the hook material 40 must be sufficiently engaged in the disposable diaper 20 to avoid separation in both a shear mode (force generally parallel to the plane of engagement) and a peel mode (force generally perpendicular to the plane of engagement) during the manufacturing and packaging processes. For example, it is desirable that the stemlike projections 48 of the hook material 40 be releasably engaged with the disposable diaper to provide a peel strength of at least about 20 grams, desirably from about 20 to about 1500 grams and more desirably from about 30 to about 90 grams. As used herein, the term "peel strength" refers to the peel strength as determined using the Peel Strength Test as set forth in conjunction with the Examples below. The peel strength values set forth above are intended to be independent of the size or shape of the hook material 40. That is, the peel strength values are not normalized to take into account the area of the hook material. It is only desired that the overall hook material, when engaged, display a peak load of failure within the above ranges.

The different embodiments of the present invention, provide a process for attaching and protecting mechanical fasteners on disposable absorbent articles and a product produced by the same. The present invention provides for the control and protection of the mechanical fasteners as the disposable absorbent articles are manufactured and packaged. This is particularly true when the mechanical fasteners are hook-and-loop type fasteners. For example, in the present invention, the stemlike projections of the hook material of the hook-and-loop type fasteners are controlled and protected to reduce or eliminate damage to the hook material during the manufacturing and packaging processes. The undamaged hook material can then provide improved fastening and refastening of the disposable absorbent articles about the waist of the wearer. Thus, the different embodiments of the present invention render the use of mechanical fasteners, such as hook-and-loop type fasteners, on disposable absorbent articles more feasible.

EXAMPLES

Peel Strength Test

This test procedure determines the peak load, measured in grams force, required to remove a hook material of a hook-and-loop type mechanical fastener from a substrate such as a disposable absorbent article. The direction of removal (peel) of the hook material from the substrate is that direction in which the hook material would generally be removed from a substrate when the product is in use. This direction is generally perpendicular to a longitudinal centerline of the product.

Equipment
1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 4201 Tensile Tester with Sintech QAD (Quality Assurance Department) Software.
2. QAD software commercially obtained from MTS Sintech under the trade designation QAD Software.
3. 90 pound per square inch grips commercially available from Instron Corporation, Canton, Mass., under the trade designation "Grips Instron 2712 (90 psi), Instron 2712-003."
4. 0.5 inch grip faces, serrated, commercially available from Instron Corporation, Canton, Mass.
5. Test facility having a temperature of 23±1° C., and a relative humidity of 50±2 percent.

Figure 12:
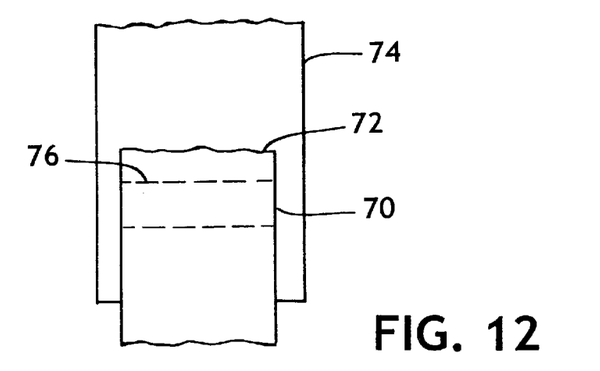
FIG. 12 illustrates a test sample for use in the peel test described below in connection with the examples.

Test Procedure
1. A sample to be tested, such as that illustrated in FIG. 12, is conditioned in the test facility for at least 4 hours prior to testing.
2. The load cell is calibrated and the QAD software loaded.
3. The grips are installed on the tensile tester with the serrated grip face being inserted into the upper jaw of the tensile tester and the jaw is closed.
4. The test condition for the tensile tester are set as follows:
   Crosshead speed: 500 millimeters/minute
   Full-scale load: 5 kilograms
   Threshold: 5 percent
   Fail criterion: 95 percent
   Gage length: 5 inches
   Hook width Direction parallel to grip face
   Hook length Direction perpendicular to grip face
5. The weight of the clamp is tared out.
6. The fingertab 72 (FIG. 12) of the fastening element is inserted into the upper jaw such that the edge of the grip face is flush with the edge 76 of the hook material 70.
7. The substrate 74 of the test sample is inserted into the lower jaw such that the hook material is positioned parallel to the edge of the lower jaw. The lower jaw is closed.
8. The crosshead is started in motion.
9. The peak load of failure is recorded. It is intended that the mode of failure is that the hook material 70 delaminates from the substrate 74. Results are rejected if the hook is torn along the edge of the grip face.

Example 1

Figure 4:
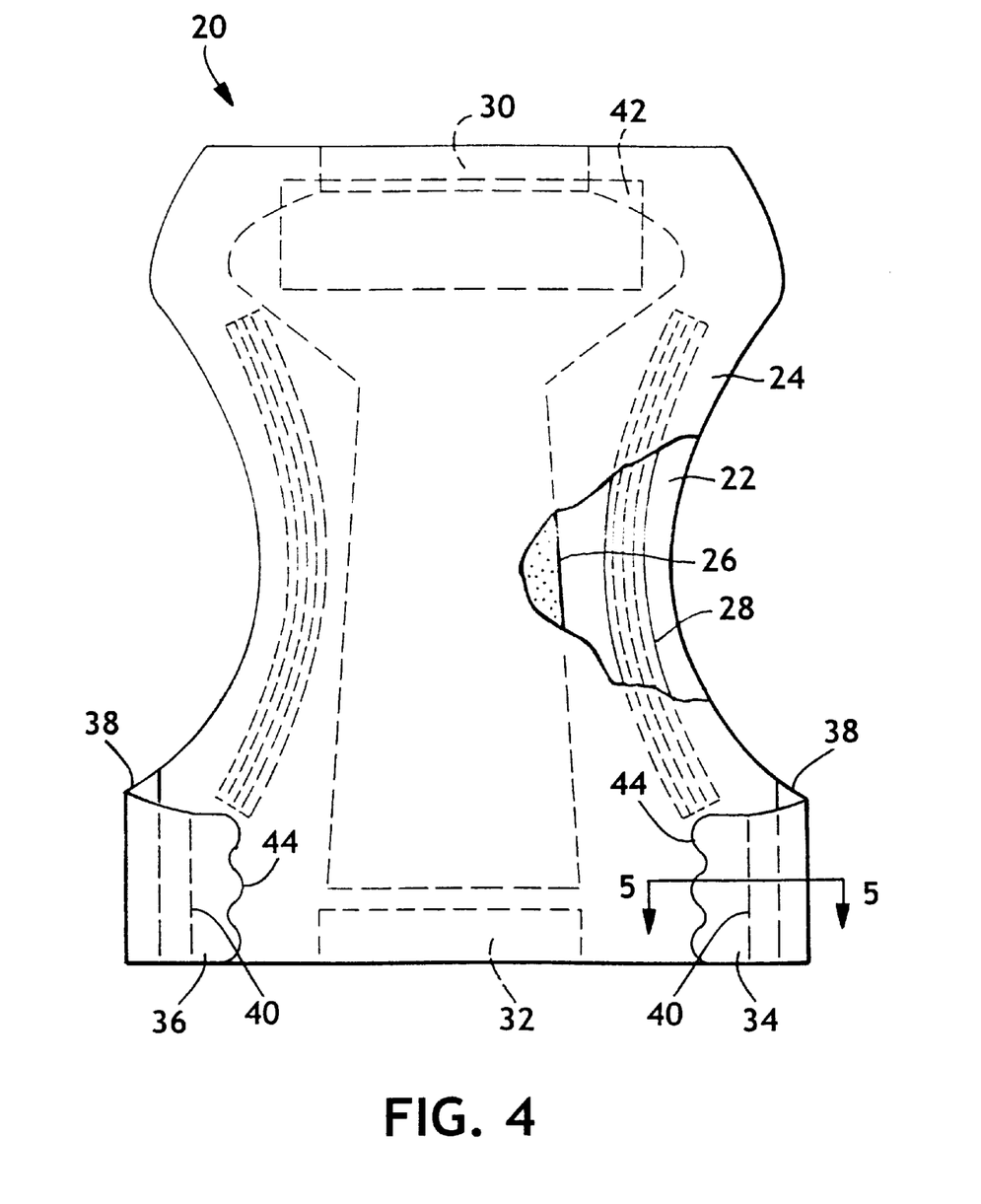
FIG. 4 is a partially cut away plan view of an absorbent article according to the present invention which illustrates an alternative attachment of the mechanical fasteners of the present invention.
Figure 5:
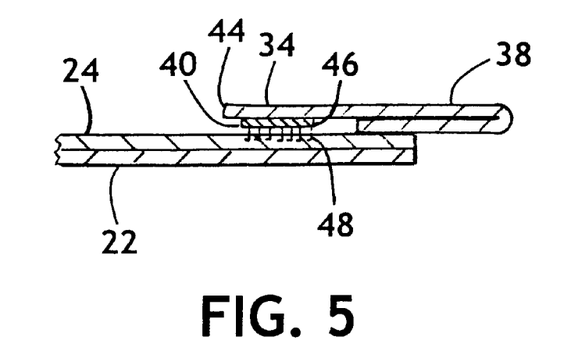
FIG. 5 is a cross-sectional view of the attachment of the mechanical fasteners as illustrated in FIG. 4 taken along line 5—5.

Ten samples of disposable diapers which are substantially the same as the diaper representatively illustrated in FIG. 4 were prepared according to the process of the present invention (commercially available Huggies® Supreme diapers; Kimberly-Clark Corporation). The diapers were removed from the package in which they had been inserted into for commercial sale. The hook material of the hook-and-loop type mechanical fastener in the diapers was commercially available from Velcro U.S.A. under the trade designation CFM-22-856. The hook material had a width of 2.00 inches and a length of 0.5 inches. The stemlike projections of the hook material were engaged with the bodyside liner before the diapers were packaged and processed according to the process of the present invention.

The bodyside liner of the disposable diaper comprises a polypropylene spunbond material having a basis weight of 0.6 ounce per square yard. The hook material was folded over and engaged with the bodyside liner of the disposable diaper by passing through a pair of nip rolls which exerted a pressure of about 100 pounds per linear inch.

The samples were then subjected to the Peel Strength Test described above. The samples had an average peel strength of 67.3 grams-force. As used herein, the term "average" refers to the sum of the tested value of two or more samples divided by the total number of samples.

Example 2

Ten samples of disposable diapers were prepared and were substantially the same as the diapers in Example 1 except that the hook material was embedded in the ear tab material, such as is representatively illustrated in FIG. 3. The diapers were removed from the package in which they had been inserted into for commercial sale. The hook material of the hook-and-loop type mechanical fastener was commercially available from Velcro U.S.A. under the trade designation CFM-22-856. The hook material had a width of 2.00 inches and a length of 0.5 inches.

The ear tab material of the disposable diaper comprises a neck bonded laminate material comprising two outer layers of a 1.2 ounce per square yard polypropylene spunbond fabric (2 denier fibers) and a center layer of a 45 gram per square meter meltblown elastomeric material (Krayton™ Styrene-butadiene block copolymer). Said laminate having a basis weight of 120 grams per square meter. The hook material was folded over and the stemlike projections of the hook material were engaged with the ear tab material by passing a roller over the hook material in one complete cycle. The roller was a 4.5 pound, rubber covered, handheld roller which was commercially available from Chemsultants International, a business having offices in Mentor, Ohio. A complete cycle is defined as one pass over the material in one direction and a second pass over the material in the opposite direction with each pass taking about one second in time. The samples were then subjected to the Peel Strength Test described above. The samples had an average peel strength of 31.2 grams-force.

Example 3

Ten samples of disposable diapers were prepared and were substantially the same as the diapers in Example 1 except that the hook material was embedded in the outer cover of the diaper, such as is representatively illustrated in FIG. 6. The diapers were removed from the package in which they had been inserted into for commercial sale. The hook material of the hook-and-loop type mechanical fastener was commercially available from Velcro U.S.A. under the trade designation CFM-22-856. The hook material had a width of 2.00 inches and a length of 0.5 inches.

The outer cover of the disposable diaper comprises a stretch thermal laminate material comprising a 0.6 mil (0.015 millimeter) polypropylene blown film and a 0.7 ounce per square yard (23.8 gsm) polypropylene spunbond material (2 denier fibers). Such a material forms the outer cover of a Huggies® Supreme diaper commercially available from Kimberly-Clark Corporation. The hook material was folded over and the stemlike projections of the hook material were engaged with the outer cover of the diaper by passing a roller over the hook material in one complete cycle. The roller was a 4.5 pound, rubber covered, handheld roller which was commercially available from Chemsultants International, a business having offices in Mentor, Ohio. A complete cycle is defined as one pass over the material in one direction and a second pass over the material in the opposite direction with each pass taking about one second in time.

The samples were then subjected to the Peel Strength Test described above. The samples had an average peel strength of 35.4 grams-force.

Example 4

Ten samples of disposable diapers were prepared and were substantially the same as the diapers in Example 1 except that the hook material was embedded in the loop material of the diaper, such as is representatively illustrated in FIG. 8. The diapers were removed from the package in which they had been inserted into for commercial sale. The hook material of the hook-and-loop type mechanical fastener was commercially available from Velcro U.S.A. under the trade designation CFM-22-856. The hook material had a width of 2.00 inches and a length of 0.5 inches.

The loop material of the disposable diaper comprises a 2 bar, warp knit fabric available from Guilford Mills, Inc., Greensborough, N.C. under the trade designation #34285. The loop material has a basis weight of 35 grams per square meter. The hook material was folded over and the stemlike projections of the hook material were engaged with the loop material of the diaper by passing a roller over the hook material in one complete cycle. The roller was a 4.5 pound, rubber covered, handheld roller which was commercially available from Chemsultants International, a business having offices in Mentor, Ohio. A complete cycle is defined as one pass over the material in one direction and a second pass over the material in the opposite direction with each pass taking about one second in time.

The samples were then subjected to the Peel Strength Test described above. The samples had an average peel strength of 453.5 grams-force. As can be seen from the examples, the process of the present invention provides adequate engagement and peel strength between the hook material and the disposable diaper to ensure that the hook material is protected during any further manufacturing and packaging processes. As can be seen, the peel strength should be at least about 20 grams force to ensure that the hook material remains engaged.

While the present invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

What is claimed is:

1. A process for attaching a mechanical fastener to a disposable absorbent article and protecting said mechanical fastener before said disposable absorbent article is handled by a user, said process comprising the following steps:

providing said disposable absorbent article which includes an outer cover, a bodyside liner, and an absorbent core disposed between said outer cover and said bodyside liner;

providing said mechanical fastener which includes a first fastening element;

attaching said first fastening element of said mechanical fastener to said disposable absorbent article;

releasably engaging said first fastening element with said outer cover of said disposable absorbent article to protect said first fastening element by passing said first fastening element and said outer cover between a pair of rotatable nip rolls wherein at least one of said rotatable nip rolls has a plurality of pins extending therefrom; and subsequently packaging said disposable absorbent article for commercial sale.

2. The process according to claim 1 wherein said step of providing said disposable absorbent article includes joining a second cooperating fastening element to said outer cover of said disposable absorbent article and wherein said first fastening element is releasably engaged with said second fastening element to protect said first fastening element prior to said step of packaging said disposable absorbent article.

3. The process according to claim 2 wherein said first fastening element is a hook material and said second fastening element is a loop material.

4. The process according to claim 1 wherein said first fastening element is a hook material of a hook and loop type fastener.

5. The process according to claim 4 wherein said hook material of said first fastening element is releasably engaged directly with said outer cover of said disposable absorbent article.

6. The process according to claim 1 wherein said first fastening element is releasably engaged with said outer cover of said disposable absorbent article to provide a peel strength of at least about 20 grams.

7. A process for attaching a hook material of a hook-and-loop type mechanical fastener to a disposable absorbent article and protecting said hook material before said disposable absorbent article is handled by a user. said process comprising the following steps:

providing said disposable absorbent article which includes an outer cover, a bodyside liner, and an absorbent core disposed between said outer cover and said bodyside liner;

providing said hook material which includes a base sheet and stemlike projections which extend from said base sheet and a loop material;

attaching said loop material and said base sheet of said hook material to said disposable absorbent article;

releasably engaging said stemlike projections of said hook material with said loop material to protect said hook material by passing said first fastening element and said outer cover between a pair of rotatable nip rolls wherein at least one of said rotatable nip rolls has a plurality of pins extending therefrom; and subsequently packaging said disposable absorbent article for commercial sale.

8. The process according to claim 7 wherein said stemlike projections are releasably engaged with said loop material to provide a peel strength of at least about 20 grams.

9. The process according to claim 7 wherein said stemlike projections are releasably engaged with said loop material to provide a peel strength of from about 30 to about 90 grams.

10. A process for attaching a pair of hook type mechanical fasteners to a disposable absorbent article and protecting said hook type mechanical fasteners before said disposable absorbent article is handled by a user, said process comprising the following steps:

providing said disposable absorbent article which includes an outer cover, a bodyside liner, an absorbent core disposed between said outer cover and said bodyside liner, and a pair of elastic ear tabs which are attached to and extend outwardly from one of said outer cover and said bodyside liner;

providing said hook type mechanical fasteners which include a base sheet and stemlike projections which extend from said base sheet;

attaching said base sheet of said hook type mechanical fasteners to said elastic ear tabs;

releasably engaging said stemlike projections of said hook type fasteners with said elastic ear tabs to protect said stem like projections by passing said stemlike projections of said hook material and said elastic ear tab between a pair of rotatable nip rolls wherein at least one of said rotatable nip rolls has a plurality of pins extending therefrom; and subsequently packaging said disposable absorbent article for commercial sale.

11. The process according to claim 10 wherein said stemlike projections are releasably engaged with said elastic ear tabs of said disposable absorbent article to provide a peel strength of at least about 20 grams.

12. A process for attaching a pair of hook type mechanical fasteners to a disposable absorbent article and protecting said hook type mechanical fasteners before said disposable absorbent article is handled by a user, said process comprising the following steps:

providing said disposable absorbent article which includes an outer cover, a bodyside liner, and an absorbent core disposed between said outer cover and said bodyside liner;

providing said hook type mechanical fasteners which include a base sheet and stemlike projections which extend from said base sheet;

attaching said base sheet of said hook type mechanical fasteners to said absorbent article;

releasably engaging said stemlike projections of said hook type fasteners with said bodyside liner to protect said stemlike projections by passing said stemlike projections of said hook material and said bodyside liner between a pair of rotatable nip rolls wherein at least one of said rotatable nip rolls has a plurality of pins extending therefrom; and subsequently packaging said disposable absorbent article for commercial sale.

13. The process according to claim 12 wherein said stemlike projections are releasably engaged with said bodyside liner of said disposable absorbent article to provide a peel strength of at least about 20 grams.

14. A process for attaching a mechanical fastener to a disposable absorbent article and protecting said mechanical fastener before said disposable absorbent article is handled by a user, said process comprising the following steps:

providing said disposable absorbent article which includes an outer cover, a bodyside liner, and an absorbent core disposed between said outer cover and said bodyside liner;

providing said mechanical fastener which includes a first fastening element;

attaching said first fastening element of said mechanical fastener to said disposable absorbent article;

releasably engaging said first fastening element with said outer cover of said disposable absorbent article to protect said first fastening element by passing said first fastening element and said outer cover between a pair of rotatable nip rolls wherein at least one of said rotatable nip rolls has a plurality of grooves therein; and subsequently packaging said disposable absorbent article for commercial sale.

15. The process according to claim 14 wherein said step of providing said disposable absorbent article includes joining a second cooperating fastening element to said outer cover of said disposable absorbent article and wherein said first fastening element is releasably engaged with said second fastening element to protect said first fastening element prior to said step of packaging said disposable absorbent article.

16. The process according to claim 15 wherein said first fastening element is a hook material and said second fastening element is a loop material.

17. The process according to claim 14 wherein said first fastening element is a hook material of a hook and loop type fastener.

18. The process according to claim 17 wherein said hook material of said first fastening element is releasably engaged directly with said outer cover of said disposable absorbent article.

19. The process according to claim 14 wherein said first fastening element is releasably engaged with said outer cover of said disposable absorbent article to provide a peel strength of at least about 20 grams.

20. A process for attaching a hook material of a hook-and-loop type mechanical fastener to a disposable absorbent article and protecting said hook material before said disposable absorbent article is handled by a user, said process comprising the following steps:

providing said disposable absorbent article which includes an outer cover, a bodyside liner, and an absorbent core disposed between said outer cover and said bodyside liner;

providing said hook material which includes a base sheet and stemlike projections which extend from said base sheet and a loop material;

attaching said loop material and said base sheet of said hook material to said disposable absorbent article;

releasably engaging said stemlike projections of said hook material with said loop material to protect said hook material by passing said first fastening element and said outer cover between a pair of rotatable nip rolls wherein at least one of said rotatable nip rolls has a plurality of grooves therein; and subsequently packaging said disposable absorbent article for commercial sale.

21. The process according to claim 20 wherein said stemlike projections are releasably engaged with said loop material to provide a peel strength of at least about 20 grams.

22. The process according to claim 20 wherein said stemlike projections are releasably engaged with said loop material to provide a peel strength of from about 30 to about 90 grams.

23. A process for attaching a pair of hook type mechanical fasteners to a disposable absorbent article and protecting said hook type mechanical fasteners before said disposable absorbent article is handled by a user, said process comprising the following steps:

providing said disposable absorbent article which includes an outer cover, a bodyside liner, an absorbent core disposed between said outer cover and said bodyside liner, and a pair of elastic ear tabs which are attached to and extend outwardly from one of said outer cover and said bodyside liner;

providing said hook type mechanical fasteners which include a base sheet and stemlike projections which extend from said base sheet;

attaching said base sheet of said hook type mechanical fasteners to said elastic ear tabs;

releasably engaging said stemlike projections of said hook type fasteners with said elastic ear tabs to protect said stemlike projections by passing said stemlike projections of said hook material and said elastic ear tab between a pair of rotatable nip rolls wherein at least one of said rotatable nip rolls has a plurality of grooves therein; and subsequently packaging said disposable absorbent article for commercial sale.

24. The process according to claim 23 wherein said stemlike projections are releasably engaged with said elastic ear tabs of said disposable absorbent article to provide a peel strength of at least about 20 grams.

25. A process for attaching a pair of hook type mechanical fasteners to a disposable absorbent article and protecting said hook type mechanical fasteners before said disposable absorbent article is handled by a user, said process comprising the following steps:

providing said disposable absorbent article which includes an outer cover, a bodyside liner, and an absorbent core disposed between said outer cover and said bodyside liner;

providing said hook type mechanical fasteners which include a base sheet and stemlike projections which extend from said base sheet;

attaching said base sheet of said hook type mechanical fasteners to said absorbent article;

releasably engaging said stemlike projections of said hook type fasteners with said bodyside liner to protect said stemlike projections by passing said stemlike projections of said hook material and said bodyside liner between a pair of rotatable nip rolls wherein at least one of said rotatable nip rolls has a plurality of grooves therein; and subsequently packaging said disposable absorbent article for commercial sale.

26. The process according to claim 25 wherein said stemlike projections are releasably engaged with said bodyside liner of said disposable absorbent article to provide a peel strength of at least about 20 grams.

* * * * *